United States Patent
Koo et al.

(10) Patent No.: US 6,952,967 B2
(45) Date of Patent: Oct. 11, 2005

(54) ULTRASONIC TRANSDUCER

(75) Inventors: Lat Sang Koo, Hamilton, OH (US);
Douglas Edward Ingram, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 253 days.

(21) Appl. No.: 10/173,760

(22) Filed: Jun. 18, 2002

(65) Prior Publication Data

US 2003/0230144 A1 Dec. 18, 2003

(51) Int. Cl.[7] ............................................. G01N 29/24
(52) U.S. Cl. ......................................... 73/632; 310/336
(58) Field of Search .......................... 73/632, 642, 629; 310/336, 334

(56) References Cited

U.S. PATENT DOCUMENTS

| | | | |
|---|---|---|---|
| 4,221,132 A | 9/1980 | Poole | 73/620 |
| 4,325,258 A | 4/1982 | Foster | |
| 4,577,506 A | 3/1986 | Poole et al. | 73/633 |
| 4,603,585 A | 8/1986 | Atalar | |
| 4,787,126 A | 11/1988 | Oliver | 29/25.35 |
| 4,800,316 A * | 1/1989 | Ju-Zhen | 310/336 |
| 4,817,016 A | 3/1989 | Thompson et al. | 364/507 |
| 5,115,414 A * | 5/1992 | Atalar et al. | 73/642 |
| 5,138,215 A | 8/1992 | Mariani | 310/313 D |
| 5,577,506 A | 11/1996 | Dias | |
| 5,681,996 A | 10/1997 | White | 73/622 |
| 5,762,066 A | 6/1998 | Law et al. | 128/660.03 |
| 5,767,408 A | 6/1998 | Lindgren et al. | 73/597 |
| 5,894,092 A | 4/1999 | Lindgren et al. | 73/598 |
| 5,974,889 A | 11/1999 | Trantow | 73/624 |
| 5,987,991 A | 11/1999 | Trantow et al. | 73/624 |
| 6,105,431 A | 8/2000 | Duffill et al. | 73/624 |
| 6,142,019 A | 11/2000 | Venchiarutti et al. | 73/602 |
| 6,190,318 B1 | 2/2001 | Bab et al. | 600/437 |

FOREIGN PATENT DOCUMENTS

GB     2 287 789 A     9/1995

OTHER PUBLICATIONS

S. Ayter, "Focusing Surface Waves Using Conical Transducers," 1987 Ultrasonics Symposium, 1987 IEEE, pp. 301–304.*

D. Frenet et al., "Generation of Leaky Rayleigh Waves Using a Conical Phased–Array Transducer: Modeling Time Domain Signals Reflected on Anisotropic Materials," 1998 IEEE Ultrasonic Symposium, 1998 IEEE, pp. 269–272.*

* cited by examiner

Primary Examiner—John E. Chapman
(74) Attorney, Agent, or Firm—V. G. Ramesvamy; Pierce Atwood

(57) ABSTRACT

An ultrasonic transducer is provided having a transduction element in the form of a truncated cone. The angle of the transduction element is selected so that the majority of the acoustic energy incident on the target is refracted beyond the longitudinal critical angle, which minimizes contamination of the inspection results.

13 Claims, 4 Drawing Sheets

US 6,952,967 B2

ULTRASONIC TRANSDUCER

BACKGROUND OF THE INVENTION

This invention relates generally to ultrasonic transducers and more particularly to ultrasonic surface acoustic wave transducers.

The use of pulse-echo ultrasonic nondestructive test methods to inspect workpieces, for example gas turbine engine components, for flaws or defects is known in the prior art. When testing workpieces by the pulse-echo ultrasonic test method, the workpiece and the transducer are typically immersed in a liquid coupling medium, such as water, for achieving good ultrasonic coupling. A transducer, for example a surface acoustic wave (SAW) transducer, produces surface waves in a target material by converting input radio frequency (RF) electric signals into acoustic waves which are directed at the workpiece, where they form surface acoustic waves. The surface waves travel along the surface of the target material and are eventually re-radiated back through the coupling medium to the SAW transducer which reconverts the acoustic waves back into output RF electric signals. The pattern of the output signals can be used to determine the presence of defects on the surface of the workpiece.

Commercially available SAW transducers are typically of hemispherical form and tend to radiate direct reflective waves in addition to surface waves. These direct reflective waves can contaminate the inspection results. These disadvantages may be ameliorated by the use of multiple transducers or phased-array transducers, however these options increase the expense of the transducers and related equipment and also complicate the transducer set-up and inspection processes.

Accordingly, there is a need for a simple SAW transducer which reduces contamination of inspection results.

BRIEF SUMMARY OF THE INVENTION

The above-mentioned need is met by the present invention, which provides an ultrasonic transducer having a transduction element in the form of a truncated cone. The angle of the transduction element relative to the target is selected so that the majority of the acoustic energy incident on the target is refracted beyond the longitudinal critical angle.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
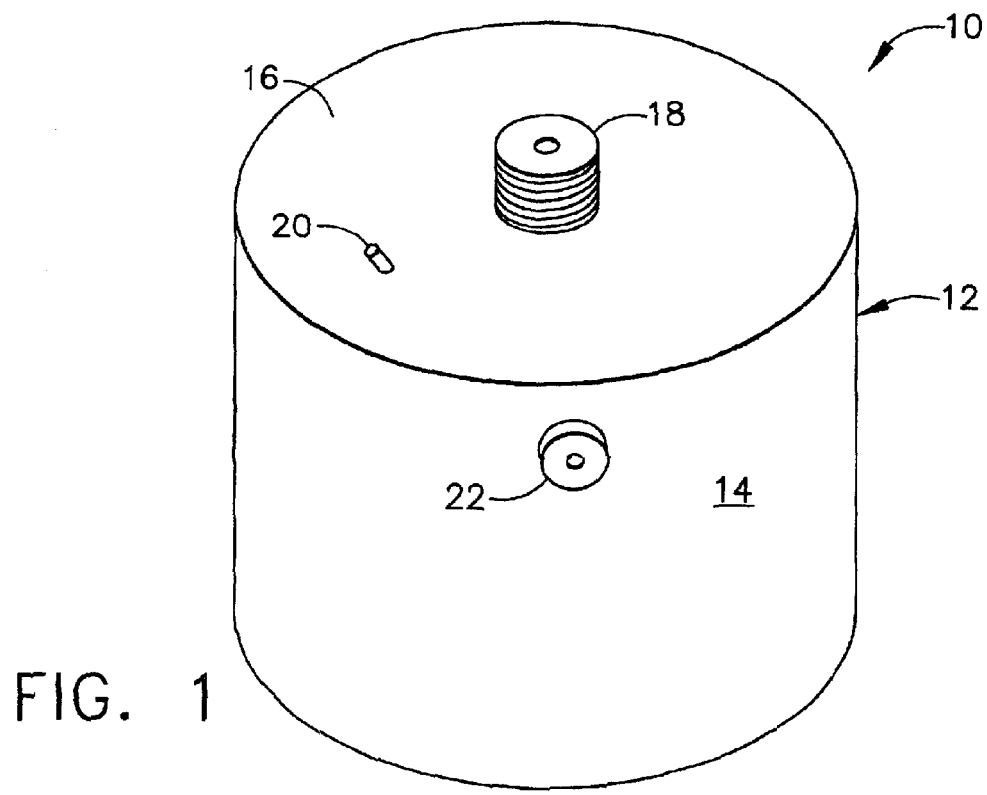
FIG. 1 is a schematic perspective view of the ultrasonic transducer of the present invention.

Referring to the drawings wherein identical reference numerals denote the same elements throughout the various views, FIG. 1 shows an exterior view of an ultrasonic transducer 10 constructed in accordance with the present invention. The transducer 10 has a cylindrical casing 12 which is closed on one end. The casing 12 itself has a side wall 14 and an end wall 16. A mechanical connector 18 extends from the end wall 16 and is used to support and manipulate the transducer 10. The end wall 16 contains a vent 20 open to an air escape tube 46, which is described in more detail below. An electrical connector 22, for example a commercially available microdot connector, is disposed in the side wall 14.

Figure 2:
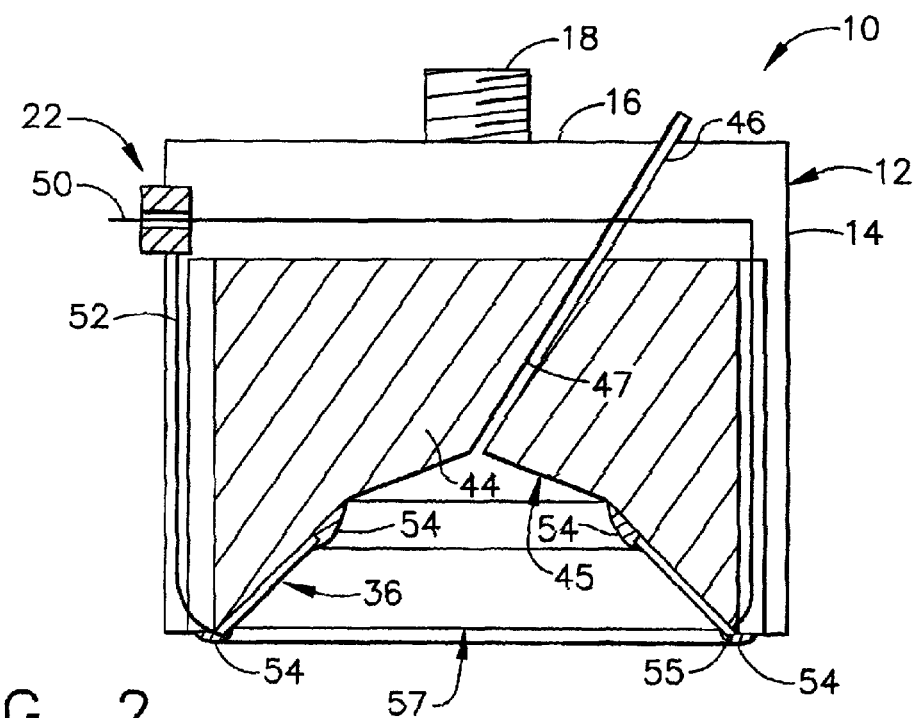
FIG. 2 is a schematic cross-sectional view of the ultrasonic transducer of FIG. 1 showing the details of its construction.

FIG. 2 is a cross-sectional view of the transducer 10 showing its construction in more detail. As discussed above, the casing 12 has a side wall 14 and an end wall 16, which may be integral with one another and may be constructed from any material which is suitable for immersion in water or other coupling medium used, for example PVC, stainless steel, or brass. A mechanical connector 18, for example a threaded connector, is attached to and extends from the surface of the end wall 16. A generally cylindrical backing 44 having a depression 45 is disposed in the center of the casing 12. The lower portion of the depression 45 is conical. The upper portion of the depression 45 serves to provide a space for air bubbles above the transduction element 36 (described below), and may be of any shape. The backing 44 is formed from epoxy, for example Astro 3060 epoxy, available from Astro Chemical Co., 3 Mill Road, Ballston Lake, N.Y. 12019. An air-escape passage 47 extends from the center of the depression 45 through the backing 44 and connects to the air-escape tube 46. A transduction element 36 in the form of a truncated circular cone is attached to the backing 44 at the outer edge of the depression 45, for example with an adhesive or epoxy. The contour of the lower portion of the depression 45 thus sets the angle of the transduction element 36 (and more particularly, its active surface 39) in relation to the side wall 14 of the casing 12, as described in more detail below. It should be noted that the transduction element 36 is depicted enlarged in its dimensions, primarily its thickness, relative to the other components of the transducer 10 in FIGS. 2, 3, 5, and 6 in order to better illustrate its structure. A circumferentially extending bottom edge 55 of the transduction element 36 defines a base plane 57, discussed in more detail below. A center lead 50 and a ground lead 52 are disposed inside the casing 12 and connect the transduction element 36 with the electrical connector 22. A sealant 54 is disposed at both ends of the transduction element 36 to seal out any water during operation of the transducer 10. One example of a suitable sealant material is 2126 sealer epoxy, available from TRA-CON, Inc., 45 Wiggins Ave., Bedford, Mass., 01730.

Figure 3:
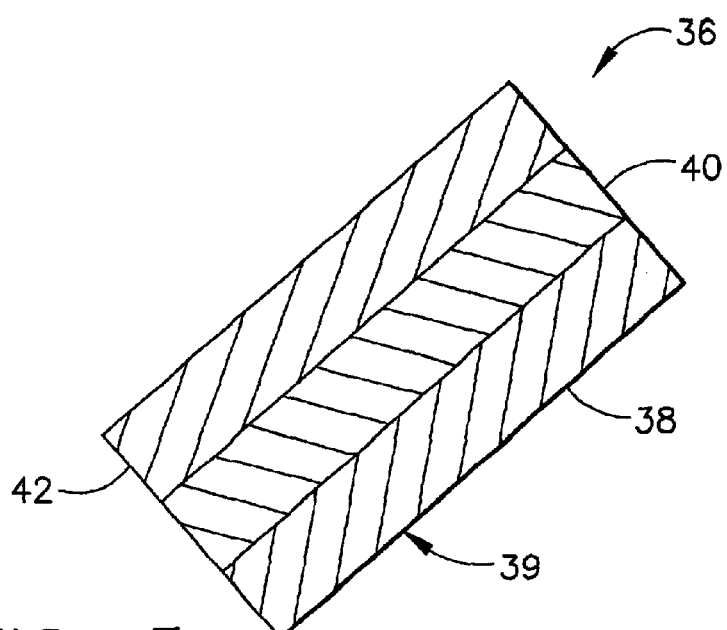
FIG. 3 is a cross-sectional view of the transduction element of the present invention.

FIG. 3 shows a more detailed view of transduction element 36. The transduction element 36 is formed from three layers. The central layer 40 is a piezoelectric material and may be formed from polyvinylidene fluoride (PVDF) film. An outer layer 38 is bonded to the central layer 40 and serves to protect the central layer 40 and to form a ground electrode connection. The outer surface of the outer layer 38 faces outward from the backing 44 and forms the active surface 39 of the transduction element 36. The outer layer 38 may be formed by metallizing the surface of the central layer 40 with gold, for example using a sputtering process. The resulting gold layer is about $1.5 \times 10^{-4}$ to $2.0 \times 10^{-4}$ mm (1500 to 2000 angstroms) thick. Other materials may be used for the outer layer 38. Whatever material is used should be electrically conductive and environmentally resistant. A backing electrode 42 serves as the backing for the middle layer 40. The backing electrode 42 is connected to an electric lead 50. The backing electrode 42 may be formed from aluminum approximately 0.127 mm (0.005 in.) thick and can be shaped as required to fit the backing 44 and then bonded to the backing 44. The backing 44 is preferably a good absorber and scatterer of acoustic energy. This reduces unwanted echo. Typically, in a practical application, the backing 44 would first be molded to the proper shape and the backing electrode 42 would be bonded to the backing 44. The middle layer 40 would then be bonded to the backing electrode, and then the outer layer 38 would be sputtered onto the middle layer 40. Finally, copper tabs and flexible wire would be used to connect the center and ground leads, 50 and 52, to the backing electrode 42 and outer layer ground electrode 38, respectively.

Figure 4:
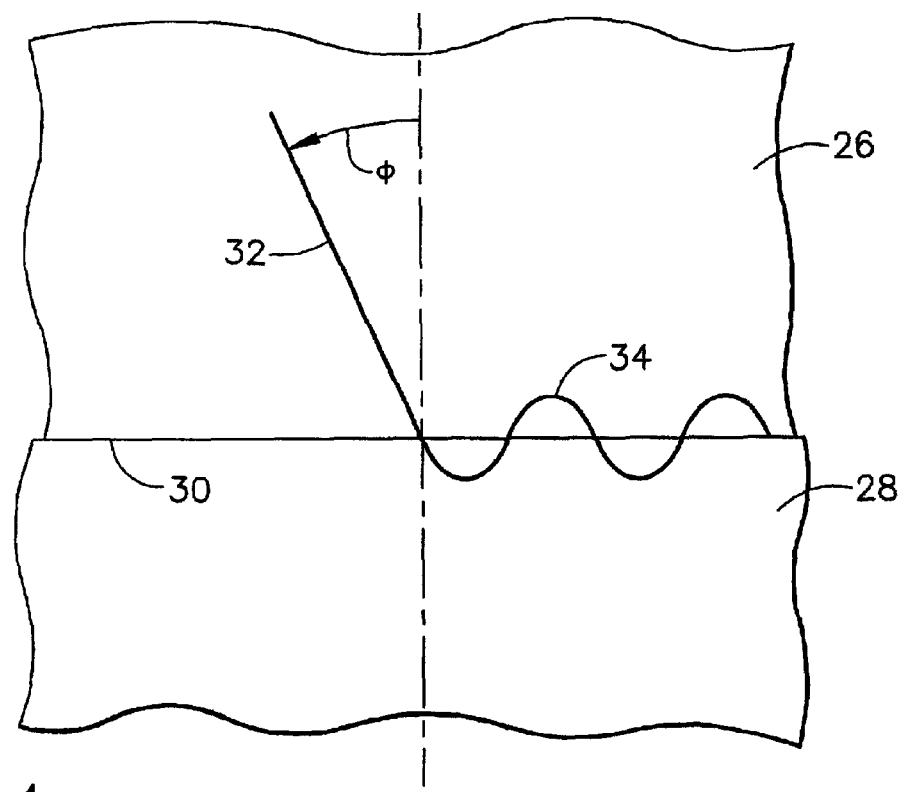
FIG. 4 is a generalized representation of the refraction of an acoustic wave in a target part.

Considering the design details of the transducer 10 in more detail, FIG. 4 depicts a generalized diagram of a first material 26 and a second material 28 which meet at an interface 30. As is known in the art, for each combination of first and second materials, there is a longitudinal critical angle measured from a line normal to the interface 30. When an incident acoustic wave 32 is directed towards the interface 30 at an angle φ equal to or greater than the critical angle, the refracted acoustic energy in the second material 28 takes the form of surface waves 34. The current invention takes advantage of this phenomenon to reduce distortions in the inspection results.

Figure 5:
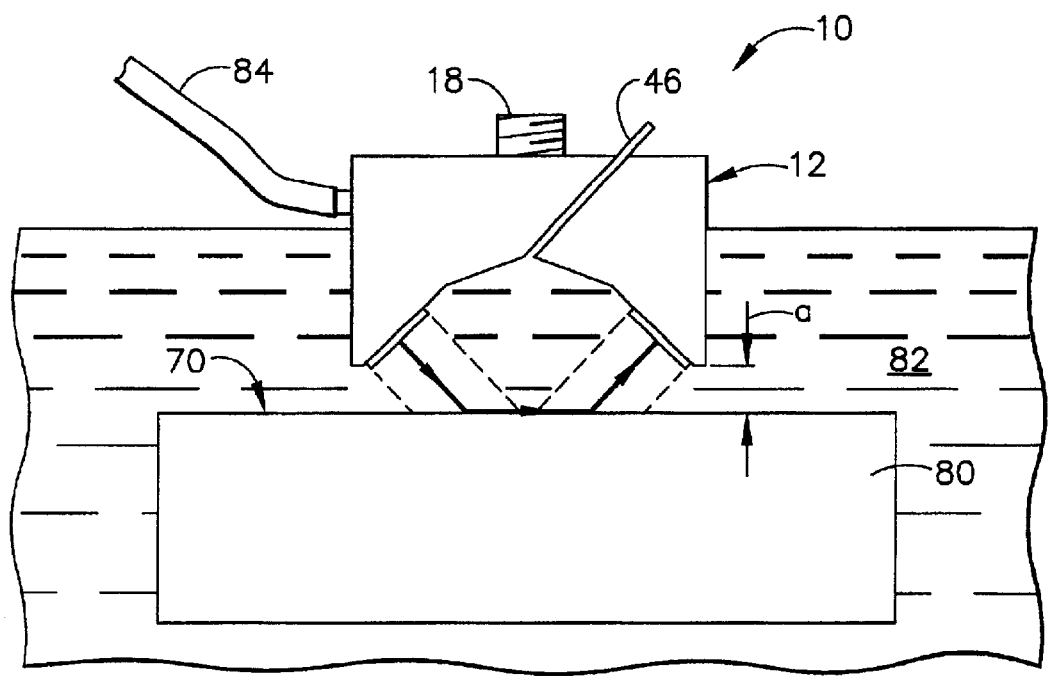
FIG. 5 is a side view representative of a target part under inspection using the present invention.

Referring to FIG. 5, in an exemplary application a target sample 80, which could be, for example, a test sample or a production component to be inspected, having a target surface 70, is immersed in a coupling medium 82, which is typically water. The transducer 10 is also immersed in the coupling medium 82, and is mechanically connected to a means of support (not shown) by mechanical connector 18. The support means may include means for suspending the transducer 10 a selected distance from the surface 70 as well as traversing the transducer 10 laterally with respect to the surface, as is known in the art. The transducer is coupled to test equipment (not shown) by a cable 84. The test equipment comprises means for generating an RF input signal for actuating the transduction element 36 to produce acoustic waves as well as means for receiving, processing, and/or displaying output signals from the transduction element 36.

Figure 6:
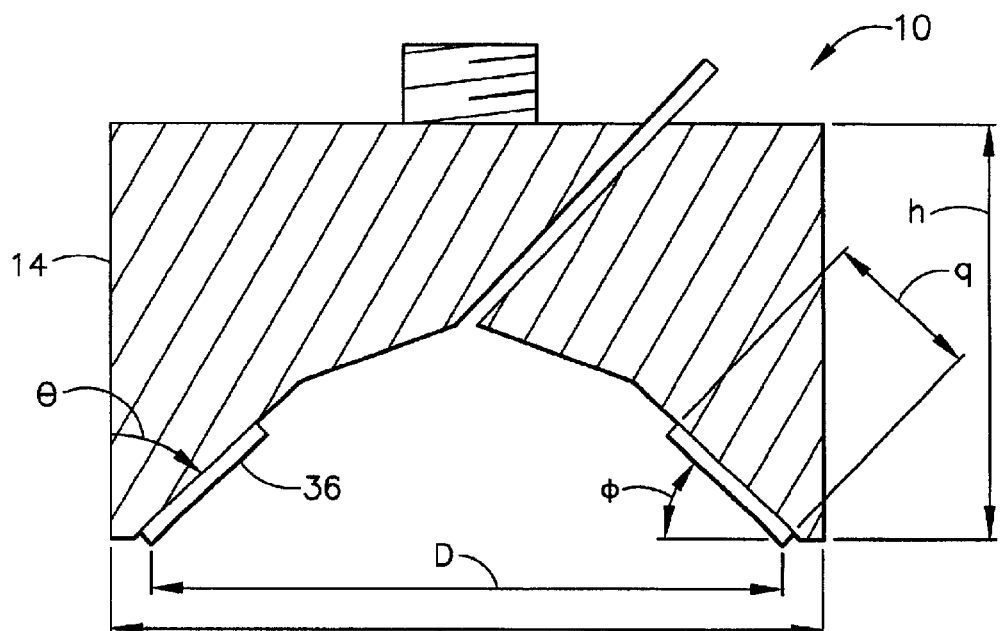
FIG. 6 is a schematic cross-sectional view of the ultrasonic transducer of FIG. 1 in operation.

Referring to FIG. 6, the transduction element 36 has an inclination angle θ with respect to the exterior sidewall 14 of the casing 12. This inclination angle is $$\theta = 90° - \phi, \tag{1}$$

where $$\phi = \sin^{-1}\left(\frac{v_m}{v}\right) \tag{2}$$

(this value of φ being the critical angle as discussed above). In equation (2), $v_m$ is the acoustical speed of the coupling medium 82 while v is the longitudinal-acoustical speed of the target sample 80, i.e. the speed at which longitudinal waves propagate through the material of the target sample 80. The transduction element 36 forms a circumferential surface of a truncated circular cone. The diameter of the base of this cone is D. The width of the transduction element 36, denoted q, for this specific geometry is based on a geometrically non-overlapping acoustic "footprint" on the interrogated surface 70 of the target part 80 and is defined by:

$$q = \frac{D}{2}\cos\phi - a\sin\phi \tag{3}$$

The variable a is the "lift-off" distance, which is the distance between the bottom surface of the transducer 10 and the target part 80, as illustrated in FIG. 5. Both the lift-off distance a and the conical diameter D may be varied to suit a particular application, keeping in mind that the farther the acoustic waves must travel through the coupling medium 82, the greater their energy loss to the medium. If the lift-off distance a is too small, the transducer will not be able to pass over protruding surface features of workpieces that are desired to be tested. If the lift-off distance a is too large, too little energy will be transferred to the target part 80. More importantly, if lift-off distance a is too large, an inspection area 86 (FIG. 7) disappears when a secondary source ring 72 (discussed below) collapses into a circular disk. By increasing the diameter D, the inspection area enclosed within the transducer 10 will be larger resulting in a reduced scan time. Once the parameters a and D are chosen, the transduction element width q can be calculated by equation (3) above. An exemplary embodiment has the following approximate dimensions: D=7.62 cm (3 in.), q=0.66 cm (0.26 in.), and θ=24.5° for $v_m$=1.483 mm/microsecond (water), v=1.63 mm/microsecond (a polyurethane material) and lift-off distance "a" chosen to be 1 cm (0.394 in.). In this example the outer diameter of the transducer 10, denoted Do, is about 9.7 cm (3.82 in.), and the height h is about 6.35 cm (2.5 in.) Both Do and h should be kept as small as possible so that the overall size of the transducer 10 will not be too large and become difficult to use on smaller targets. The angle θ should be equal to or less than the calculated value from equation (1), so as to minimize the acoustic energy that is transmitted other than as surface waves. It is noted that since the acoustic waves are emitted normal to the surface of the transduction element 36, angle φ is also equal to the angle between the surface of the target sample 80 and the active surface 39 of the transduction element 36, as shown in FIG. 6. It is further noted that, in operation the transducer 10 is placed in relation to the target part 80 so that the base plane 57 is parallel to the target surface of the target part 80. Therefore, the angle between the transduction element active surface 39 and the workpiece target surface 70 is also equal to the angle φ between the active surface 39 and the base plane 57. The critical angle varies with the material of the target part 80 and a new transducer 10 is required for each combination of coupling medium 82 and target part material to be tested. This is facilitated by the simplicity of fabrication of the transducer 10 of the present invention.

It should be noted that, in theory, surface waves are generated whenever the angle φ is about equal to the critical angle or greater than the critical angle. In the illustrated example the angle φ is selected to be substantially equal to the calculated critical angle. In actual practice, the angle φ may vary because of expected manufacturing tolerances, for example, it may be on the order of about 5 degrees less to about 5 degrees more than the selected angle. This does not unacceptably degrade the performance of the transducer 10.

Figure 7:
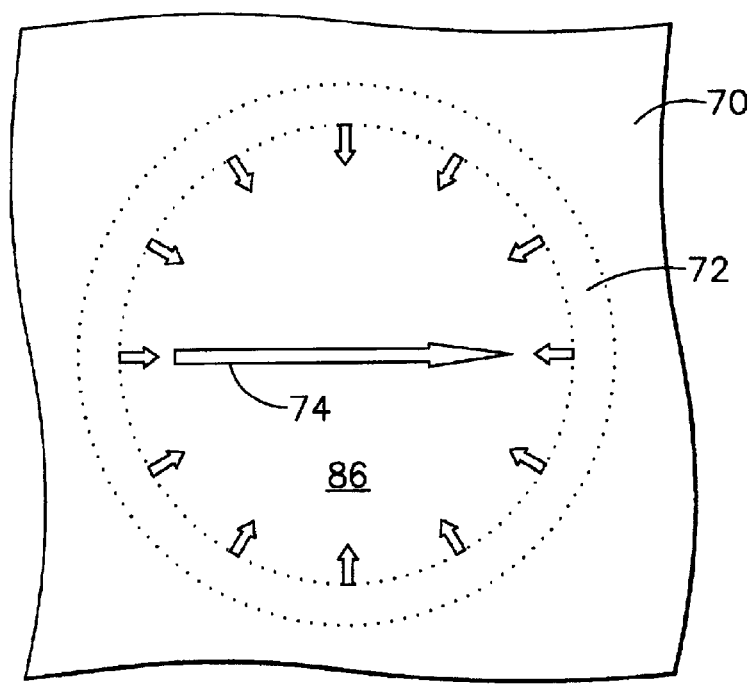
FIG. 7 is a top view representative of a portion of a target part under inspection using the present invention.
Figure 8:
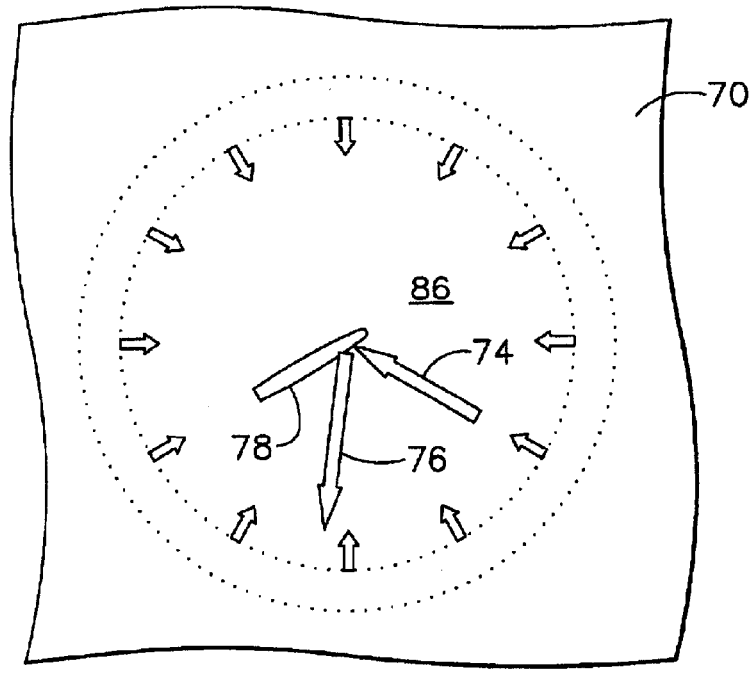
FIG. 8 is a top view representative of a portion of a target part under inspection using the present invention.

In operation, the transducer 10 is used to generate acoustical waves on the surface 70 of a target sample 80, as shown in FIGS. 7 and 8. In this example, and in typical practical applications, water is used as the coupling medium 82. An acoustic wave is generated at the transduction element 36, which then travels through the coupling medium 82 toward the surface of the sample 70. Once it hits the sample's surface, it creates a secondary, surface acoustic source on the sample 70. This secondary source has a shape of a circular ring 72 on the sample surface 70 as is shown in FIGS. 7 and 8. This ring 72 circumscribes a circular disk area 86 which is the inspection area for the transducer 10 at its current location. As the transducer 10 is moved in a scan pattern along one edge of the target sample 80 with a gradual step along the other edge, the whole surface 70 will be covered. At each transducer location, the created surface wave travels forward and radiates energy constantly back to the coupling medium 82 and eventually back to the opposite side of the transduction element 36 if the wave is within or at the edge of the ring 72. When there is no surface defect within the inspection area, the transmitted wave, one general direction of which is denoted by arrow 74, moves forward without any interruption as is depicted in FIG. 7. However if there is a surface defect 78 within the inspection area, the transmitted wave 74 will be reflected and scattered by the defect resulting in a different form and shape, as denoted by arrow 76 in FIG. 8. The change, in form and shape of the surface wave 72 is collected with the transduction element 36.

The foregoing has described an ultrasonic transducer having a truncated cone transduction element that reduces contamination of inspection results. While specific embodiments of the present invention have been described, it will be apparent to those skilled in the art that various modifications thereto can be made without departing from the spirit and scope of the invention as defined in the appended claims.

What is claimed is:

1. An ultrasonic transducer comprising a transduction element formed into a ring and inclined so as to define a truncated conical shape having an open interior, said transduction element having a bottom edge which defines a base plane, and having an active surface, wherein said active surface is disposed at an angle $\phi$ with respect to said base plane such that, during operation of said ultrasonic transducer, substantially all of the acoustic energy incident upon a surface of a target will be refracted as surface waves, wherein said active surface of said transduction element has a width q, said width being equal to:

$$q = \frac{D}{2}\cos\phi - a\sin\phi$$

wherein D is an outer diameter of said transduction element, and a is a lift-off distance from said bottom edge of said transduction element to said surface of said target.

2. The ultrasonic transducer of claim 1, wherein $\phi$ is no less than about:

$$\sin^{-1}\left(\frac{v_m}{v}\right)$$

wherein v is equa to the longitudinal acoustic velocity of said target to be tested and $v_m$ is equal to the acoustic velocity of a coupling medium to be used to acoustically couple said transduction element and said target.

3. The ultrasonic transducer of claim 1, wherein $\phi$ is substantially equal to:

$$\sin^{-1}\left(\frac{v_m}{v}\right)$$

wherein v is equal to the longitudinal acoustic velocity of said target to be tested and $v_m$ is equal to the acoustic velocity of a coupling medium to be used to acoustically couple said transduction element and said target.

4. An ultrasonic transducer for inspecting a surface of a target, comprising:
a generally cylindrical casing having a closed end and an internal cavity, said cavity having an opening opposite said closed end and said closed end having an air escape tube;
a backing disposed in said cavity, said backing having a generally conical depression facing said opening and an air escape passage that connects to said air escape tube; and
a generally circular transduction element comprising a piezoelectric material attached to said backing at an outer edge of said generally conical depression, said transduction element being formed in the shape of a truncated cone and having a bottom edge defining a base plane, wherein an active surface of said transduction element is disposed at an angle $\phi$ with respect to said base plane such that, during operation of said ultrasonic transducer, substantially all of the acoustic energy incident upon said surface of said target will be refracted as surface waves.

5. The ultrasonic transducer of claim 4 wherein $\phi$ is no less than about:

$$\sin^{-1}\left(\frac{v_m}{v}\right)$$

wherein v is equal to the longitudinal acoustic velocity of said target and $v_m$ is equal to the acoustic velocity of a coupling medium to be used to acoustically couple said transduction element and said target.

6. The ultrasonic transducer of claim 5 wherein said transduction element comprises a backing layer, a central piezoelectric layer, and an outer layer.

7. The ultrasonic transducer of claim 5 wherein said active surface of said transduction element has a width q, said width being equal to:

$$q = \frac{D}{2}\cos\phi - a\sin\phi$$

wherein D is an outer diameter of said transduction element, and a is a lift-oft distance from a bottom edge of said transduction element to said surface of said target.

8. The ultrasonic transducer of claim 4 wherein $\phi$ is substantially equal to:

$$\sin^{-1}\left(\frac{v_m}{v}\right)$$

wherein v is equal to the longitudinal acoustic velocity of said target to be tested and $v_m$ is equal to the acoustic velocity of a coupling medium to be used to acoustically couple said transduction element and said target.

9. The ultrasonic transducer of claim 4 wherein said backing is formed from epoxy.

10. A method of ultrasonically inspecting a target comprising:
providing a coupling medium;
placing a target having a surface to be inspected in said coupling medium; and providing a transducer having a transduction element formed into a ring and inclined so as to define a truncated conical shape having an open interior, a bottom edge defining a base plane, and an active surface, wherein said active surface is disposed at an angle φ with respect to said base plane, such that, during operation of said ultrasonic transducer, substantially all of the acoustic energy incident upon a surface of said target will be refracted as surface waves, wherein said active surface of said transduction element has a width q, said width being equal to:

$$q = \frac{D}{2}\cos\phi - a\sin\phi$$

wherein D is an outer diameter of said transduction element, and a is a lift-off distance from a bottom edge of said transduction element to said surface of said target.

11. The method of claim 10 wherein φ is no less than about:

$$\sin^{-1}\left(\frac{v_m}{v}\right)$$

wherein v is equal to the longitudinal acoustic velocity of said target to be tested and $v_m$ is equal to the acoustic velocity of a coupling medium to be used to acoustically couple said transduction element and said target;

generating acoustic waves using said transducer, wherein said generated acoustic waves travel through said coupling medium, contact said surface of said target, and cause the creation of surface acoustic waves in said target which traverse said surface of said target and radiate into said coupling medium; and receiving said radiated acoustic waves in said transducer.

12. The method of ultrasonically inspecting a target according to claim 11 wherein said generated acoustic waves contact said surface of said target in a generally circular, non-overlapping pattern.

13. The method of claim 10, wherein φ is substantially equal to:

$$\sin^{-1}\left(\frac{v_m}{v}\right)$$

wherein v is equal to the longitudinal acoustic velocity of said target to be tested and $v_m$ is equal to the acoustic velocity of a coupling medium to be used to acoustically couple said transduction element and said target.

* * * * *

UNITED STATES PATENT AND TRADEMARK OFFICE
CERTIFICATE OF CORRECTION

PATENT NO.         : 6,952,967 B2                                            Page 1 of 1
APPLICATION NO. : 10/173760
DATED              : October 11, 2005
INVENTOR(S)       : Koo et al.

It is certified that error appears in the above-identified patent and that said Letters Patent is hereby corrected as shown below:

In Claim 2, column 5, line 64, delete "is equa to" and insert therefor -- is equal to --.
In Claim 7, column 6, line 49, delete "lift-oft" and insert therefor -- lift-off --.

Signed and Sealed this

Thirteenth Day of November, 2007

JON W. DUDAS
*Director of the United States Patent and Trademark Office*